(12) United States Patent
Curcillo

(10) Patent No.: US 9,597,061 B2
(45) Date of Patent: Mar. 21, 2017

(54) METHOD FOR INSERTING MEDICAL INSTRUMENT

(71) Applicant: The Institute for Cancer Research, Philadelphia, PA (US)

(72) Inventor: Paul Curcillo, Philadelphia, PA (US)

(73) Assignee: The Institute for Cancer Research, Philadelphia, PA (US)

( * ) Notice: Subject to any disclaimer, the term of this patent is extended or adjusted under 35 U.S.C. 154(b) by 350 days.

(21) Appl. No.: 14/046,630

(22) Filed: Oct. 4, 2013

(65) Prior Publication Data

US 2014/0100431 A1    Apr. 10, 2014

Related U.S. Application Data

(60) Provisional application No. 61/710,576, filed on Oct. 5, 2012.

(51) Int. Cl.
  *A61B 17/00* (2006.01)
  *A61B 17/34* (2006.01)
  *A61B 1/06* (2006.01)

(52) U.S. Cl.
  CPC ............... *A61B 17/00* (2013.01); *A61B 1/06* (2013.01); *A61B 1/0661* (2013.01); *A61B 17/34* (2013.01); *A61B 17/3417* (2013.01); *A61B 17/3421* (2013.01); *A61B 17/3423* (2013.01); *A61B 90/30* (2016.02); *A61B 2017/347* (2013.01); *A61B 2017/348* (2013.01); *A61B 2017/349* (2013.01); *A61B 2017/3482* (2013.01); *A61B 2017/3484* (2013.01); *A61B 2017/3486* (2013.01); *A61B 2017/3488* (2013.01); *A61B 2017/3492* (2013.01)

(58) Field of Classification Search
  CPC ......... A61B 1/06; A61B 1/0661; A61B 17/00; A61B 17/34; A61B 17/3417; A61B 17/3421; A61B 17/3423; A61B 2017/347; A61B 2017/348; A61B 2017/3482; A61B 2017/3484; A61B 2017/3486; A61B 2017/3488; A61B 2017/349; A61B 2017/3492; A61B 19/52; A61B 19/5202
  See application file for complete search history.

(56) References Cited

U.S. PATENT DOCUMENTS

| 7,070,586 B2 * | 7/2006 | Hart | A61B 17/3417 604/164.04 |
|---|---|---|---|
| 2014/0005474 A1 * | 1/2014 | Farin | A61B 1/00154 600/104 |

FOREIGN PATENT DOCUMENTS

JP    10-137184 A    5/1998

* cited by examiner

*Primary Examiner* — Larry E Waggle, Jr.
(74) *Attorney, Agent, or Firm* — Birch, Stewart, Kolasch & Birch, LLP

(57) ABSTRACT

To reliably fix a medical instrument to a body wall by easy operation without causing increased costs and complicated configuration. For inserting a trocar as a medical instrument which can be pierced into a body cavity, a front end of the trocar is inserted into a body wall along a first direction having a specified angle with respect to an exterior surface of the body wall, and then the front end of the trocar is inserted into the body wall along a second direction whose angle with the exterior surface of the body wall is acuter than that of the first direction. As a result, the trocar is reliably fixed with large resistance received from the body wall.

9 Claims, 17 Drawing Sheets

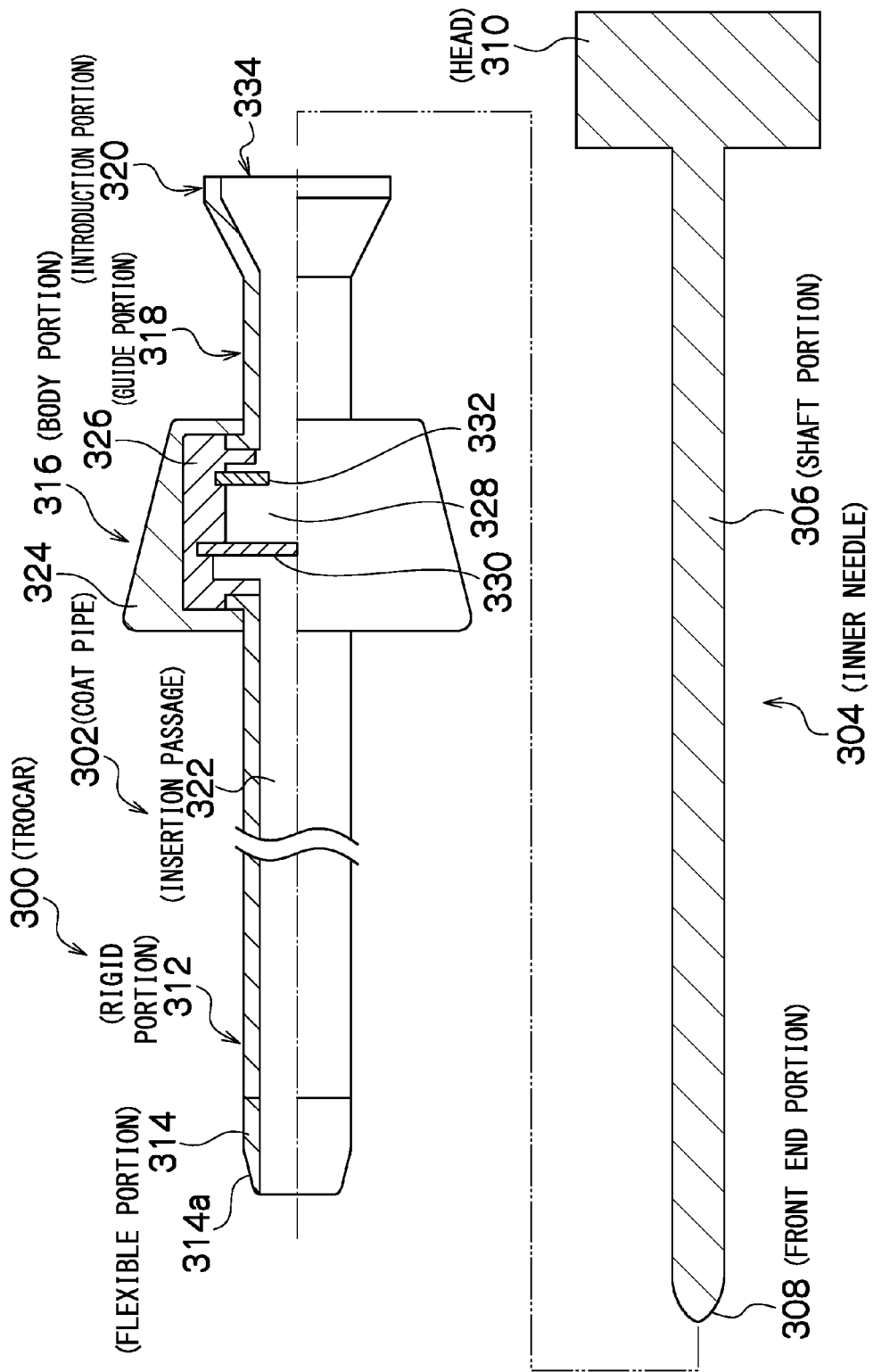

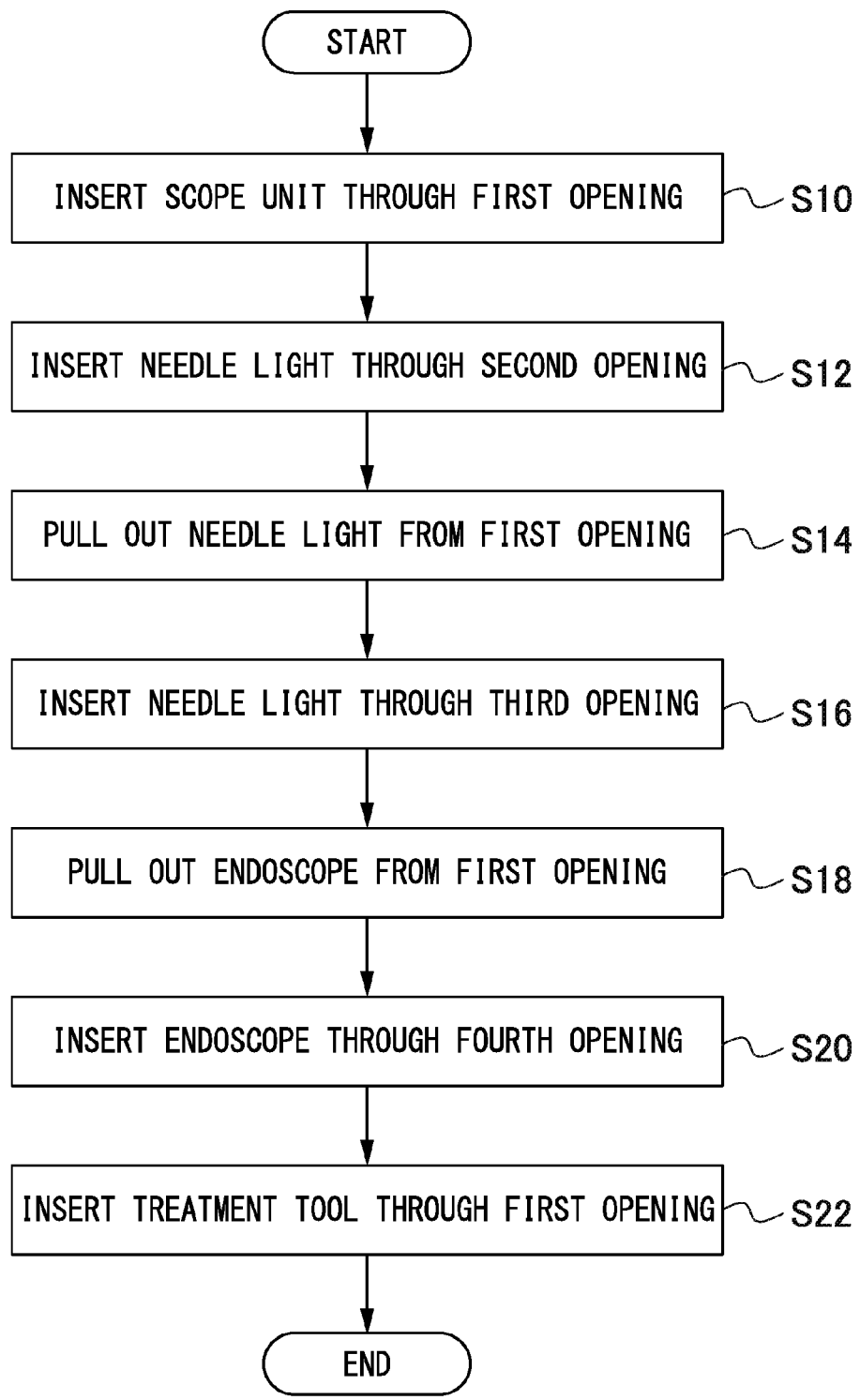

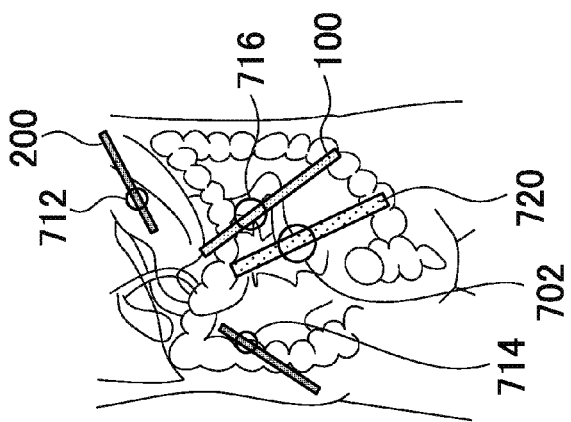
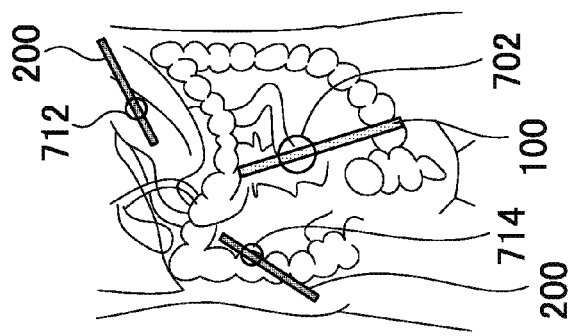
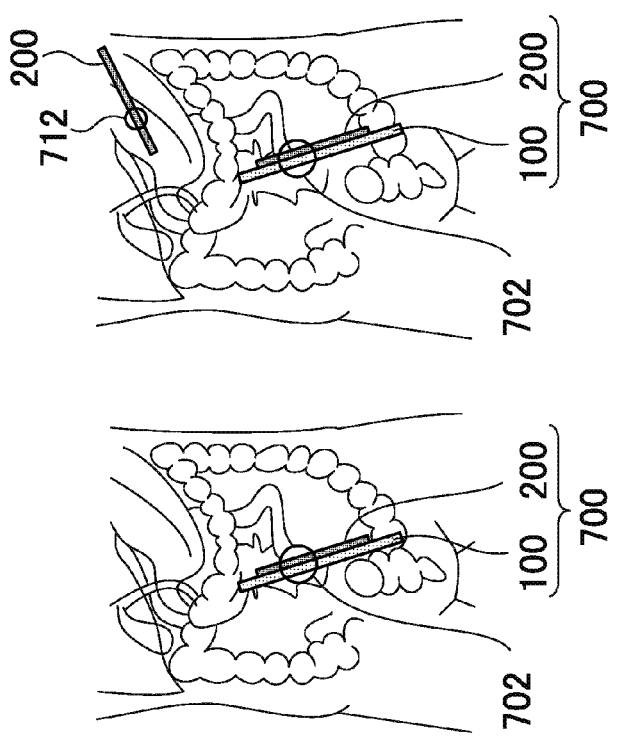

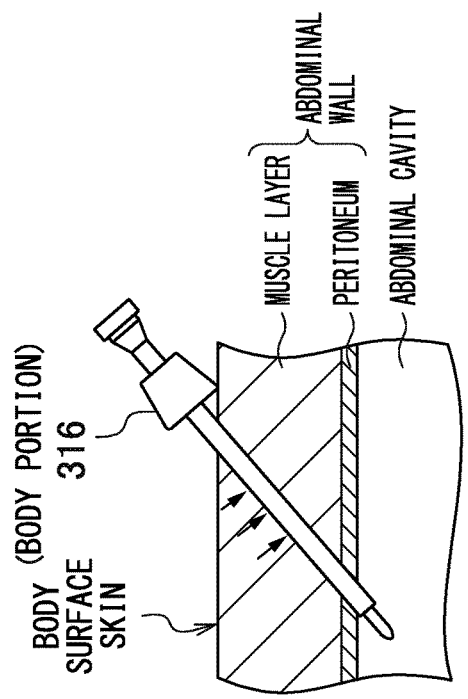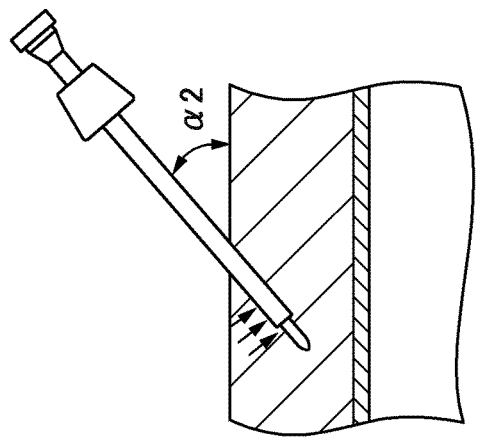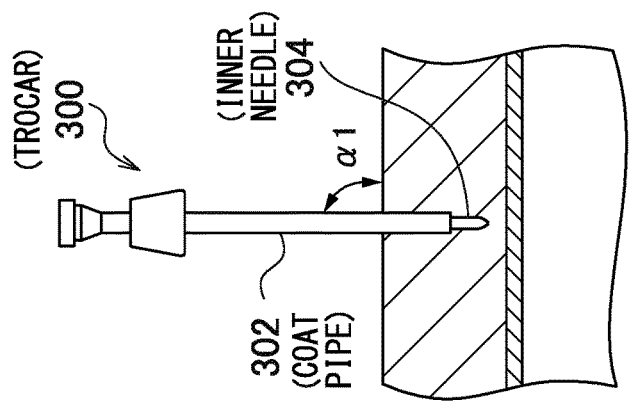

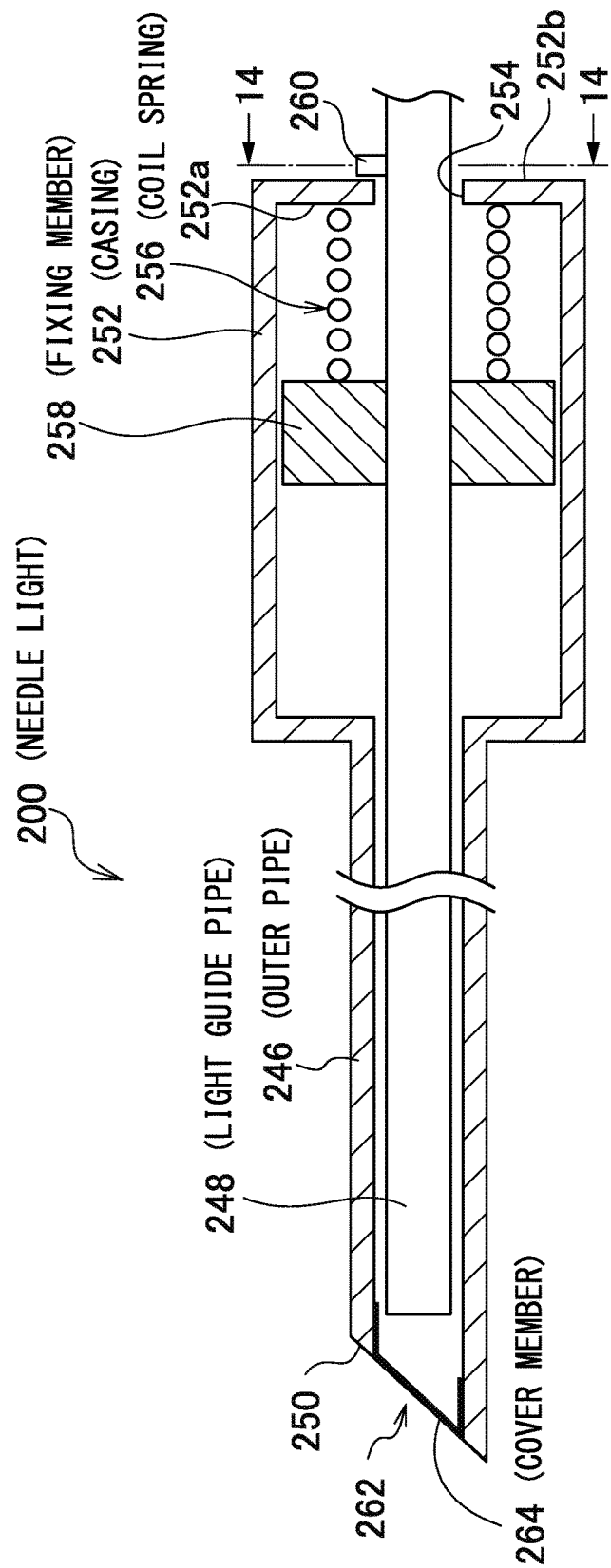

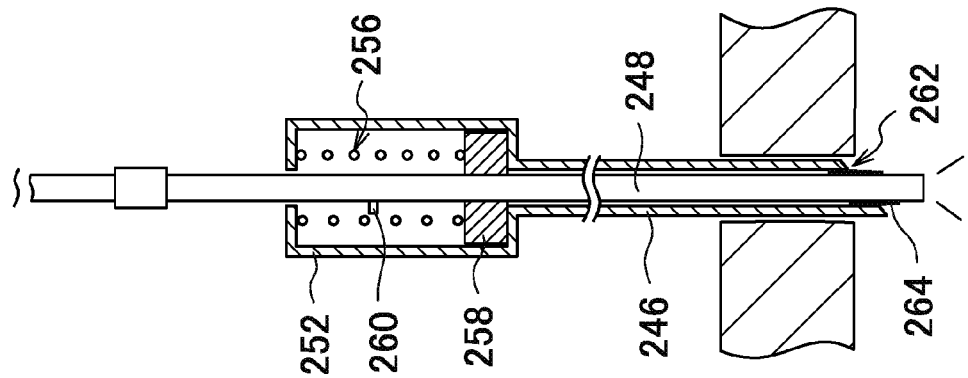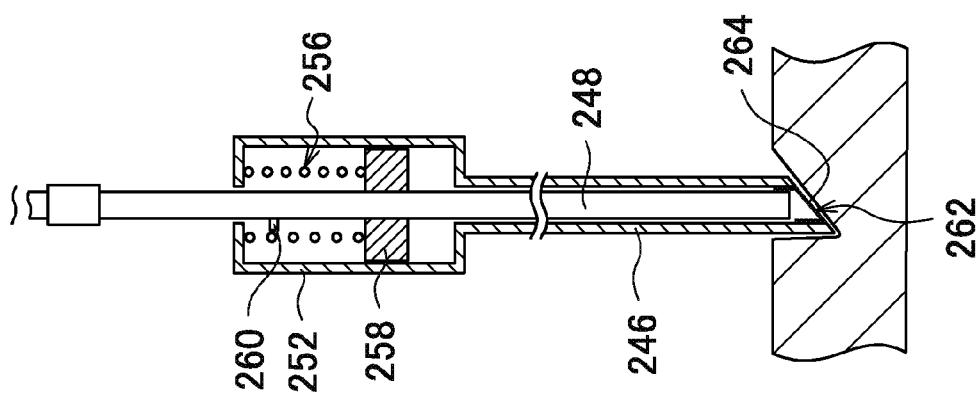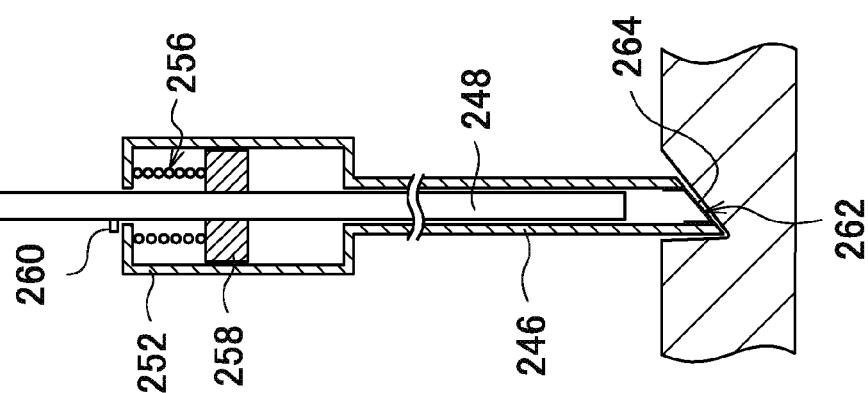

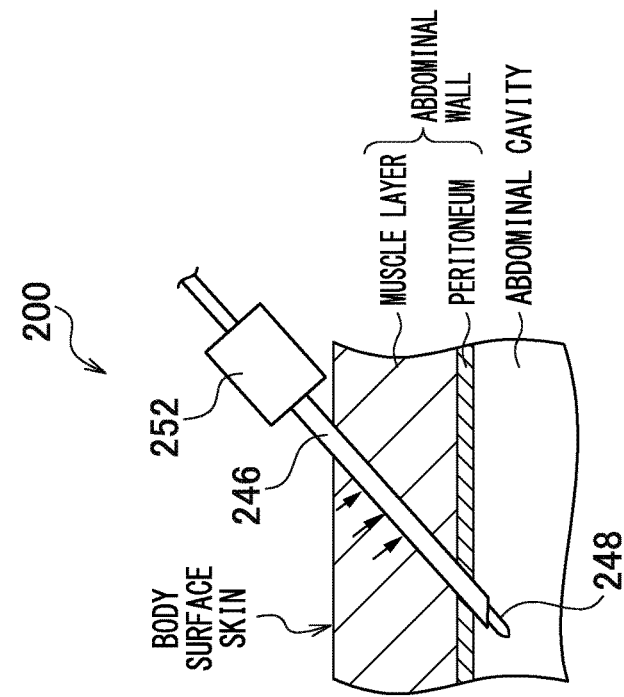
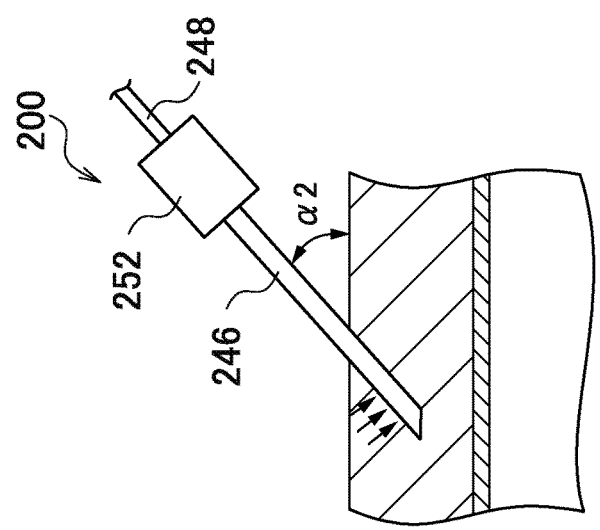
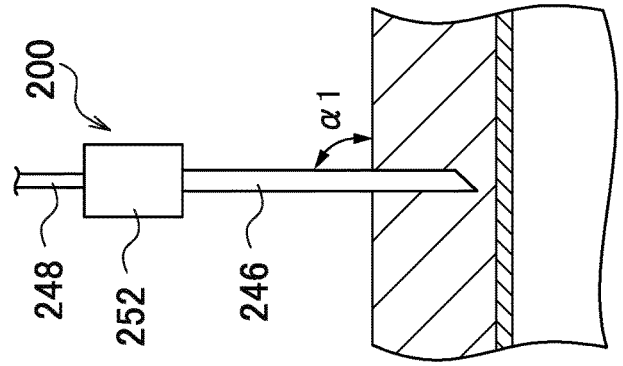

METHOD FOR INSERTING MEDICAL INSTRUMENT

CROSS REFERENCE TO RELATED APPLICATIONS

This application claims priority under U.S.C. §119(e) of U.S. Provisional Applications 61/710,576 filed on Oct. 5, 2012 which is incorporated herein by reference in its entirety.

BACKGROUND OF THE INVENTION

Field of the Invention

The present invention relates to a method for inserting a medical instrument and more particularly relates to a technology for fixing to a body wall a medical instrument which can be pierced into a body cavity.

Description of the Related Art

In recent years, endoscopic surgery using a rigid endoscope (rigid mirror) such as an abdominoscope is widely performed since the endoscopic surgery is less invasive to a patient than surgery involving operation such as laparotomy and thoracotomy. For example, in laparoscopic surgery, a cylindrical trocar is pierced into several places on an abdominal region of a patient, and an endoscope (abdominoscope), treatment tools and the like are inserted into an abdominal cavity through the trocar, so that treatment is performed with use of the treatment tools while an endoscope image is observed with a monitor.

Recently, single port surgery (SPS) that is laparoscopic surgery performed with one hole formed on an umbilical region is also rapidly spreading. Since only one postoperative scar is left in an umbilical region in the single port surgery, it is less distinctive, and therefore the surgery is excellent in terms of cosmetics.

However, in the single port surgery, only one opening (insertion hole) is formed on a body wall for access into a body cavity, the endoscope and the treatment tools tend to interfere inside and outside the body cavity, which tends to constrain operation of these tools. When the endoscope and the treatment tools interfere, it may become impossible to position the endoscope at a location convenient for observation, which may hinder observation and treatment of a treatment target region.

Under these circumstances, a demand for reduction in diameter of an insertion portion of the endoscope is increasing. If the diameter of the insertion portion of the endoscope can be reduced, an opening for the endoscope can be downsized even when it is formed in portions other than the umbilical region, so that a postoperative scar can be made less noticeable. Moreover, it becomes possible to solve failures in the aspect of operation and observation as compared with the case of accessing into a body cavity through one opening.

Generally, the endoscope has a function of observing an inside of a body cavity as well as a function of illuminating the inside of the body cavity. More specifically, a light guide for transmitting illumination light from a light source device is inserted to and placed at an insertion portion of the endoscope. The illumination light emitted from an emitting end of the light guide is made to irradiate the inside of the body cavity through an illumination window. Accordingly, if the insertion portion of the endoscope is made too small, enough occupation space for inserting and placing the light guide is not secured, which causes insufficient brightness of the illumination light.

On the other hand, Japanese Patent Application Laid-Open No. 10-137184 discloses a system including an endoscope to observe an inside of a body cavity and an illuminator (illumination probe) configured separately from the endoscope to illuminate the inside of the body cavity. According to the system, even when the illumination light emitted from the endoscope has insufficient brightness, desired brightness can be obtained by the illumination light emitted from the illuminator. Moreover, since an observation position can be irradiated with the illumination light from various directions, it becomes much easier to observe the observation position.

When the illuminator inserted into a body cavity is not reliably fixed to a body wall, the illuminator is easily shaken by slight body motions and external vibrations, which makes illumination inside the body cavity unstable and hinders observation and treatment inside the body cavity. There is also a possibility that the front end of the illuminator may cause organ damage. It may be considered to newly provide a means to fix the illuminator to the body wall, though it is not preferable as it may lead to increased costs and complicated configuration.

In Japanese Patent Application Laid-Open No. 10-137184, attention is not at all paid to reliable fixing of the illuminator inserted into a body cavity to a body wall, so that the above-stated problem cannot be solved.

The present invention has been made under such circumstances, and an object of the present invention is to provide a method for inserting a medical instrument so that the medical instrument can reliably be fixed to a body wall by easy operation without causing increased costs and complicated configuration.

SUMMARY OF THE INVENTION

In order to accomplish the above object, a method for inserting a medical instrument according to the present invention is a method for inserting a medical instrument which can be pierced into a body cavity, including: a first insertion step of inserting a front end of the medical instrument into a body wall along a first direction having a specified angle with respect to an exterior surface of the body wall; and a second insertion step of inserting, after execution of the first insertion step, the front end of the medical instrument into the body wall along a second direction whose angle with respect to the exterior surface of the body wall is acuter than that of the first direction.

In the present invention, "the first direction" is preferably a direction generally vertical to the exterior surface of the body wall. More specifically, the angle of the first direction formed with the exterior surface of the body wall is preferably 70 degrees to 110 degrees, more preferably 80 degrees to 100 degrees, and specifically preferably 85 degrees to 95 degrees.

In the present invention, the first insertion step is preferably a step of inserting the front end of the medical instrument from the exterior surface of the body wall to a middle position inside the body wall. The second insertion step is preferably a step of inserting the front end of the medical instrument from the middle position inside the body wall to the inside of the body cavity.

In a preferable aspect of the present invention, the angle of the second direction formed with the exterior surface of the body wall is 60 degrees or less. In a more preferable aspect, the angle of the second direction with respect to the exterior surface of the body wall is 45 degrees or less, and is more preferably 30 degrees or less.

In a preferable aspect of the present invention, the medical instrument is a guide pipe having an insertion passage for guiding a body-cavity insertion instrument into the body cavity. In a more preferable aspect, the body-cavity insertion instrument is an illuminator for illuminating the inside of the body cavity.

In a preferable aspect of the present invention, the medical instrument is an illuminator for illuminating the inside of the body cavity. In a more preferable aspect, the illuminator includes: a cylindrical outer pipe having a front end opening with a sharp front end; an illumination member inserted into the outer pipe movably along a shaft direction so as to be able to emit illumination light from a front end portion of the illumination member; a biasing member for biasing the illumination member in a front end direction with respect to the outer pipe; a locking member for locking movement of the illumination member in the front end direction in a state where the front end portion of the illumination member is housed in the outer pipe against biasing force of the biasing member; and a protective cover for closing the front end opening of the outer pipe in a state where the front end portion of the illumination member is housed in the outer pipe by the locking member, and if a front end of the outer pipe is not in contact with a body tissue when locking by the locking member is unlocked, the front end portion of the illumination member pushes away the protective cover and projects from the front end opening of the outer pipe in the front end direction with the biasing force of the biasing member.

According to the present invention, the front end of the medical instrument, which can be pierced into a body cavity, is inserted into a body wall along the first direction. Then, the insertion direction is changed to the second direction whose angle is acuter than that of the first direction, and in this direction, the front end of the medical instrument is further inserted into the body wall. As a result, the medical instrument is fixed with large resistance received from the body wall. This makes it possible to reliably fix the medical instrument to the body wall by easy operation without causing increased costs and complicated configuration.

BRIEF DESCRIPTION OF THE DRAWINGS

FIG. 4 is a schematic view showing a configuration example of a trocar;

FIG. 5 is a flowchart showing procedures for inserting body-cavity insertion instruments into an abdominal cavity;

FIGS. 6A to 6D are plan views schematically showing the body-cavity insertion instruments being inserted into an abdominal cavity;

FIGS. 12A to 12C are explanatory views showing a method for inserting a trocar;

FIG. 13 is a schematic view showing a configuration example of a needle light according to a second embodiment;

FIGS. 16A to 16C are explanatory views showing the needle light according to the second embodiment being inserted into an abdominal wall;

FIGS. 18A to 18C are explanatory views showing a method for inserting the needle light according to the second embodiment.

DETAILED DESCRIPTION OF THE PREFERRED EMBODIMENTS

Hereinafter, preferable embodiments of the present invention are described in detail with reference to accompanying drawings.

First Embodiment

[Medical Observation System]

Figure 1:
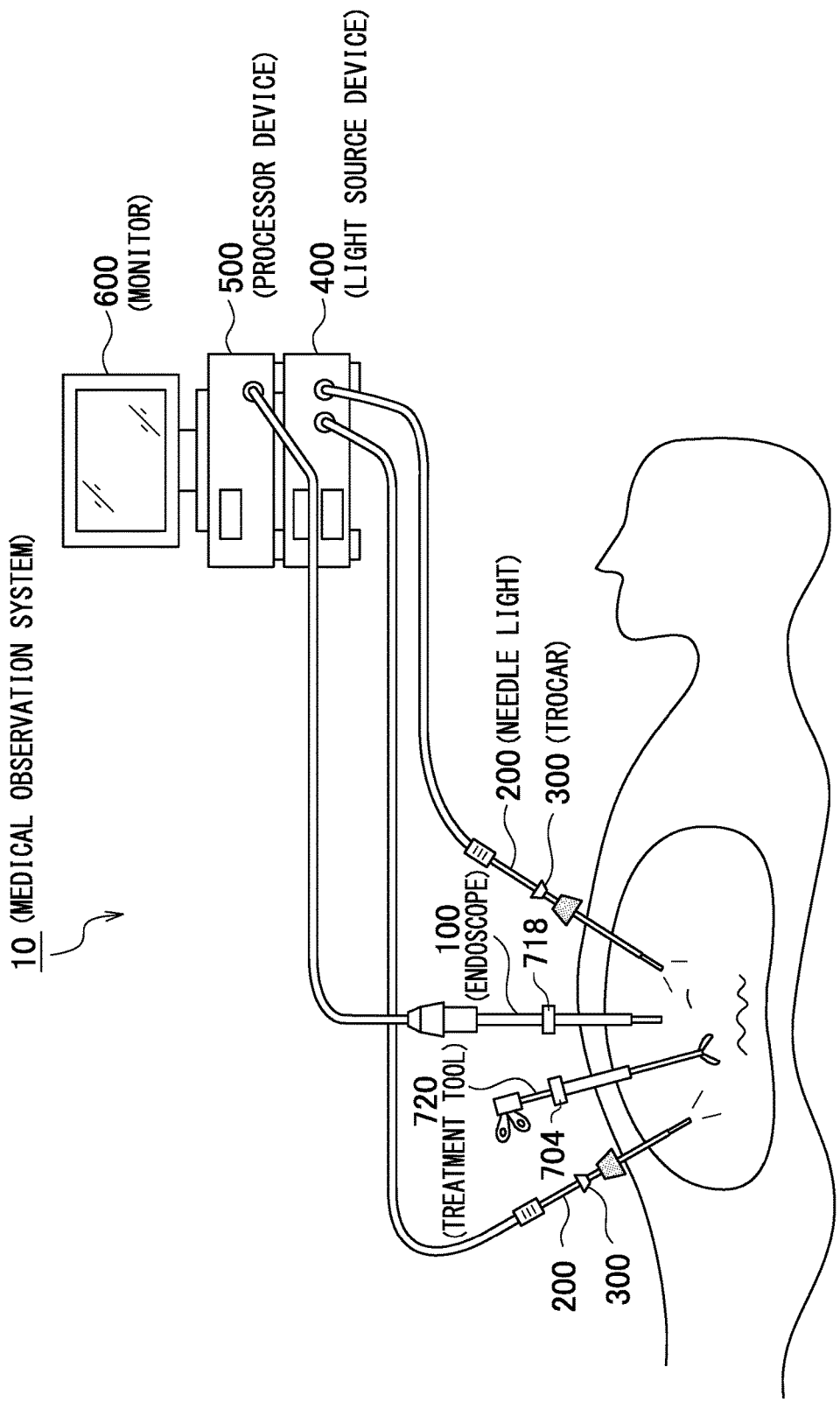
FIG. 1 is an overall configuration view showing one embodiment of a medical observation system.

FIG. 1 is an overall configuration view showing one embodiment of a medical observation system. As shown in FIG. 1, the medical observation system 10 of the present embodiment includes an endoscope 100 inserted into a body cavity, for observing an observation target portion in a body cavity, a needle light (illuminator) 200 inserted into a body cavity, for irradiating a body cavity of a subject with illumination light, a light source device 400 for feeding illumination light to the needle light 200, and a processor device 500 for generating an endoscope image. The processor device 500 is connected to a monitor 600 for displaying the endoscope image.

[Endoscope]

Figure 2:
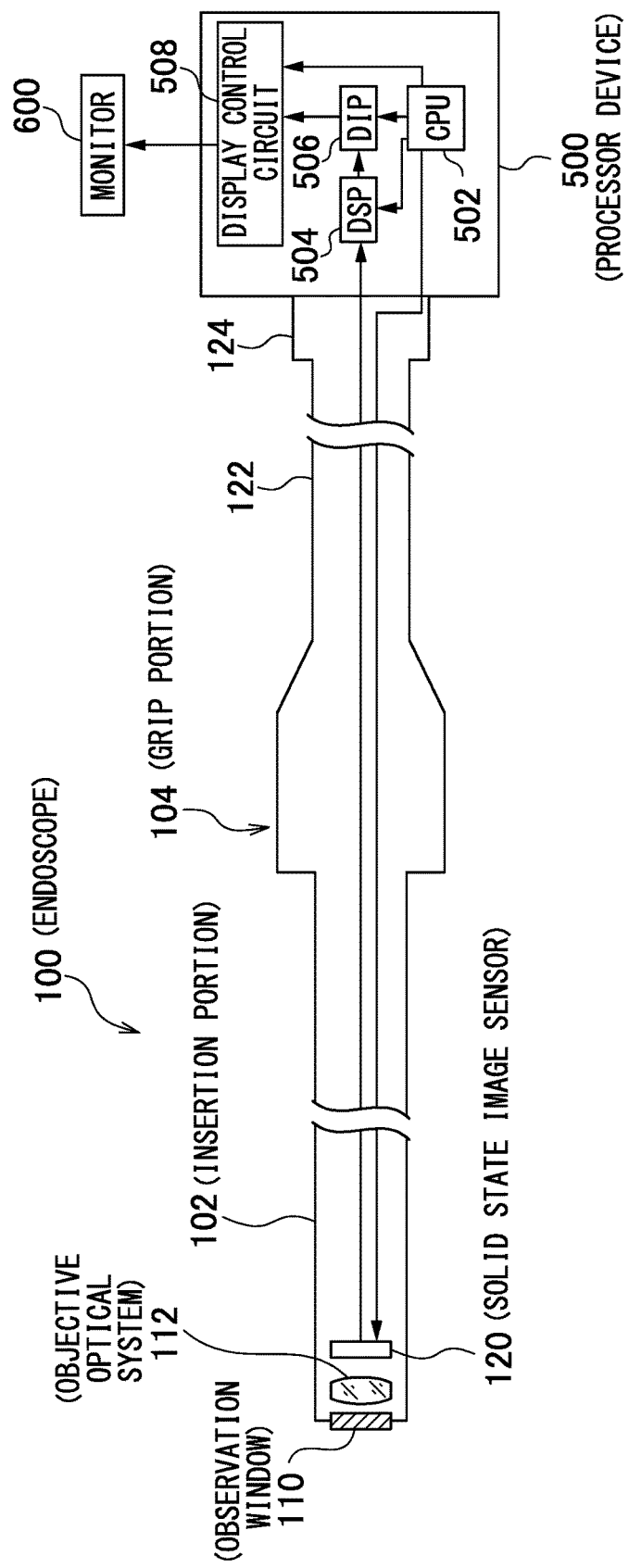
FIG. 2 is a schematic view showing a configuration example of an endoscope.

FIG. 2 is a schematic view showing a configuration example of the endoscope 100. The endoscope (electronic endoscope) 100 shown in FIG. 2 includes a rigid insertion portion 102 that is inserted into a body cavity of the subject, a grip portion 104 provided in a back end of the insertion portion 102, and a signal cable 122 extendedly provided from the back end of the grip portion 104. At the end of the signal cable 122, a connector 124 removably connected to the processor device 500 is provided.

An observation window 110 for taking in image light of an object is mounted on the front end of the insertion portion 102. Behind the observation window 110, an objective optical system 112 and a solid state image sensor 120 (such as a CMOS sensor and a CCD sensor) are placed. Object light passing through the observation window 110 and the objective optical system 112 is incident into an imaging surface (light receiving surface) of the solid state image sensor 120. The solid state image sensor 120 performs photoelectric conversion of the incident object light, and outputs a converted electrical signal (imaging signal). The electrical signal outputted from the solid state image sensor 120 is inputted into the processor device 500 through the signal cable 122 and the connector 124.

As shown in FIG. 2, the processor device 500 includes a CPU 502, a DSP 504, a DIP 506 and a display control circuit 508. The CPU 502 integrally controls operation of the entire processor device 500.

The DSP 504 performs various signal processings, such as color separation, color interpolation, gain correction, white balance adjustment, and gamma control, on the electrical signal outputted from the solid state image sensor 120 to generate image data. The image data generated in the DSP 504 is inputted into the DIP (digital image processing circuit) 506.

The DIP 506 performs electronic variable magnification, or various image processings such as color enhancement and edge enhancement, on the image data processed in the DSP 504. The image data subjected to various image processings in the DIP 506 is inputted into the display control circuit 508.

The display control circuit 508 converts the image data from the DIP 506 into a video signal corresponding to a signal format supported by the monitor 600, and outputs it to the monitor 600. As a consequence, an observed image (endoscope image) is displayed on the monitor 600.

In the present embodiment, the insertion portion 102 of the endoscope 100 does not include an illumination means for illuminating an inside of a body cavity. That is, the insertion portion 102 does not have an illumination window and a light guide which are included in common endoscopes. As a result, an occupation space for placing these members is unnecessary. Accordingly, an external diameter of the insertion portion 102 can be reduced, so that an opening (insertion hole) formed on a body wall for guiding the insertion portion 102 into a body cavity can be downsized. This makes it possible to make a postoperative scar less noticeable and to thereby reduce the burden on the subject.

In the present embodiment, an external diameter of the insertion portion 102 is preferably 3 mm or less. In this example, the external diameter of the insertion portion 102 is set to 2.9 mm. By setting the external diameter of the insertion portion 102 to 3 mm or less, an opening (insertion hole) formed on a body wall for guiding the insertion portion 102 into the body cavity can be downsized. As a result, it becomes unnecessary to suture the opening and therefore a postoperative scar can be made less noticeable. If the external diameter of the insertion portion 102 is made too small, a sufficient occupation space for built-in objects (such as an image guide) that are built in the inside of the insertion portion 102 cannot be secured. It is preferable, therefore, that the external diameter of the insertion portion 102 is 2 mm or more.

Although the endoscope 100 is constituted of an electronic endoscope (electronic scope) in the present embodiment, it may also be constituted of an optical endoscope (fiberscope).

[Needle Light]

Figure 3:
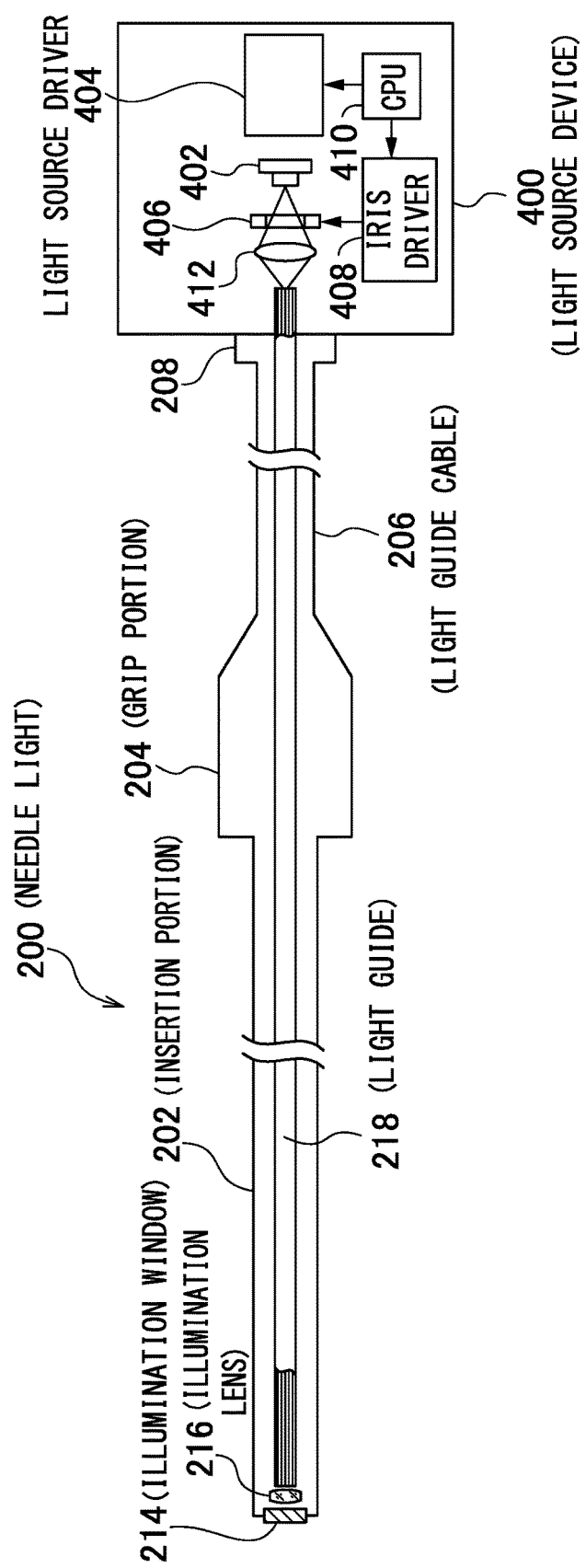
FIG. 3 is a schematic view showing a configuration example of a needle light.

FIG. 3 is a schematic view showing a configuration example of the needle light 200. As shown in FIG. 3, the needle light 200 includes an insertion portion 202 that is inserted into a body cavity, a grip portion 204 provided in a back end of the insertion portion 202, and a light guide cable 206 extendedly provided from the back end of the grip portion 204. At the end of the light guide cable 206, a light source connector 208 removably connected to the light source device 400 is provided.

The insertion portion 202 is made of an oblong cylindrical member having flexibility, with an illumination window 214 being mounted on a front end surface of the insertion portion 202. Behind the illumination window 214, an illumination lens 216 is placed for emitting illumination light toward the inside of the body cavity. The illumination lens 216 faces an emitting end of a light guide 218. The light guide 218 is inserted into the insertion portion 202, the grip portion 204, and the light guide cable 206, so that an incident end thereof is exposed from the end of the light source connector 208. When the light source connector 208 is connected to the light source device 400, the incident end of the light guide 218 is inserted into the light source device 400. The illumination light from the light source device 400 is guided by the light guide 218 to the front end portion 212 so as to irradiate the inside of the body cavity through the illumination lens 216 and the illumination window 214.

As shown in FIG. 3, the light source device 400 includes a light source 402, a light source driver 404, an aperture adjustment mechanism 406, an iris driver 408, and a CPU 410 which controls these component members. The light source 402 is turned on and off under control of the light source driver 404 and emits illumination light toward a condenser lens 412 positioned ahead. As the light source 402, a xenon lamp, a halogen lamp, an LED (light emitting diode), a fluorescent light emitting element, or an LD (laser diode) can be used for example. The light source 402 is properly selected depending on the type of an endoscope image (visible image, fluorescence images and the like) to be picked up, i.e., depending on a wavelength to be used.

The aperture adjustment mechanism 406 is placed between the light source 402 and the condenser lens 412 to adjust a light volume of the illumination light so that an endoscope image picked up by the solid state image sensor 120 (see FIG. 2) of the endoscope 100 has generally constant brightness. The aperture adjustment mechanism 406 includes an aperture blade, which changes a diameter of an aperture opening (aperture diameter) for passing the illumination light, and a motor for driving the aperture blade. The iris driver 408 opens and closes the aperture blade of the aperture adjustment mechanism 406 to change a passage area of the illumination light so as to adjust the light volume of the illumination light incident into the light guide 218.

In the present embodiment, an external diameter of the insertion portion 202 is preferably 3 mm or less, and more preferably 2.3 mm or less. In this example, the external diameter of the insertion portion 202 is 2.1 mm. Consequently, as in the case of the insertion portion 102 of the endoscope 100, an opening (insertion hole) formed on a body wall for guiding the insertion portion 202 into a body cavity can be downsized, and thereby a postoperative scar can be made less noticeable.

Moreover, in the present embodiment, the needle light 200 is shown to be configured such that the illumination light from the light source device 400 is guided to the front end portion of the insertion portion 202 by the light guide 218 and is emitted to the inside of the body cavity through the illumination lens 216 and the illumination window 214. However, without being limited thereto, the configuration of the needle light may be such that an LED light source is built in the top end of the needle light.

[Trocar]

FIG. 4 is a schematic view showing a configuration example of a trocar 300. As shown in FIG. 4, the trocar 300, which is a guide member for guiding the needle light 200 into a body cavity, includes a coat pipe 302 and an inner needle 304.

The inner needle 304, which is to be inserted into the coat pipe 302, includes a shaft portion 306 formed to be oblong, a front end portion 308 formed at the front end of the shaft portion 306, and a head 310 provided on the base end side of the shaft portion 306. In this example, the shaft portion 306 of the inner needle 304 has an external diameter of 2.1 mm.

The front end portion 308 is dulled into a curved surface shape having no edge (i.e., formed into a roundish non-edge shape) while being capable of easily penetrating a body wall. The shaft portion 306 has an external diameter slightly smaller than an inner diameter of the coat pipe 302. The head 310 is formed into a cylindrical shape which is thicker than the shaft portion 306. When the inner needle 304 is inserted into the coat pipe 302, the head 310 is brought into contact with an end face of the base end side of the coat pipe 302 with the front end portion 308 of the inner needle 304 projecting by a prescribed length from the front end of the coat pipe 302.

The coat pipe 302 includes an oblong rigid portion 312 formed from hard resin, metal and the like, an flexible portion 314 coupled to the front end side of the rigid portion 312, a body portion 316 coupled to the base end side of the rigid portion 312, a guide portion 318 coupled to the base end side of the body portion 316, and an introduction portion 320 provided on the base end side of the guide portion 318. The rigid portion 312, the flexible portion 314, the body portion 316, the guide portion 318, and the introduction portion 320 are coaxially placed, with an insertion passage 322 formed inside these portions so that the needle light 200 and the inner needle 304 can be inserted therein. In this example, the rigid portion 312 has an external diameter of 2.3 mm.

The flexible portion 314 is formed of a flexible member such as rubber and flexible resin. The flexible portion 314 may be made of the same material as the rigid portion 312 (i.e., hard resin, metal and the like), and may be configured to have a plurality of slits (thin grooves) formed on its outer periphery in a circumferential direction or a shaft direction, or in other directions so that the flexible portion 314 is more flexible than the rigid portion 312. A front end portion 314a of the flexible portion 314 is formed in a tapered shape with a thickness continuously decreased over a prescribed length, so that flexibility (plasticity) is higher on the front end side. In addition, corners of the front end portion 314a are formed into a roundish non-edge shape. Therefore, when the flexible portion 314 placed at the front end part of the coat pipe 302 comes into contact with an organ in the state where the inner needle 304 has been pulled out from the coat pipe 302 stuck into a body cavity, damage of the organ can be prevented since the flexible portion 314 deforms itself because of its flexibility.

The rigid portion 312 is a portion formed in a region which is to be enclosed with a body wall when the coat pipe 302 is stuck into a body cavity. The rigid portion 312 is formed of a hard member such as hard resin and metal. Therefore, when the trocar 300 is fed to a prescribed position inside a body cavity and then the inner needle 304 is pulled out from the coat pipe 302, the coat pipe 302 receives pressure force from the body wall, but the rigid portion 312 prevents the coat pipe 302 from being deformed by the pressure force. Accordingly, it becomes possible to smoothly insert the needle light 200 into the coat pipe 302.

The body portion 316 includes an elastic body layer 324 provided on the entire surface of the body portion 316 and an inner pipe portion 326 provided inside the elastic body layer 324.

The elastic body layer 324 is, for example, made of an elastic member such as rubber and sponge. Since the elastic body layer 324 functions as a means to absorb pressure exerted on a patient, it is preferably formed with a relatively large thickness. As a consequence, when the coat pipe 302 is stuck into a body cavity and the body portion 316 of the coat pipe 302 is in contact with a body wall for a long time and thereby applies pressure thereto, the elastic body layer 324 absorbs and alleviates the pressure. This makes it possible to reduce the burden to the patient and to achieve low invasiveness.

The inner pipe portion 326 is formed of a hard member such as hard resin and metal as in the case of the rigid portion 312. The inner pipe portion 326 may be configured integrally with the rigid portion 312, and may be configured separately. In the latter case, the inner pipe portion 326 and the rigid portion 312 are coupled with adhesives, solder and the like.

Formed in the inner pipe portion 326 is an inner pipe way 328 which constitutes a part of the insertion passage 322. The inner pipe way 328 has a check valve 330 and a sealing member 332 provided side by side in a shaft direction. The check valve 330 is for preventing compressed air in the body cavity from leaking out of the body in the state where the needle light 200 or the inner needle 304 has been pulled out of the coat pipe 302. The sealing member 332 is placed much closer to the base end side than the check valve 330 for sealing a clearance between the needle light 200 or the inner needle 304 and the inner pipe way 328 when the inner needle 304 or the needle light 200 is inserted into the coat pipe 302. The check valve 330 and the sealing member 332 are, for example, made of an elastic member such as rubber.

The guide portion 318 is configured to have an inner diameter slightly larger than an external diameter of the insertion portion 202 of the needle light 200 and to have a sufficient length in the shaft direction. Accordingly, when the front end portion of the insertion portion 202 receives large resistance from the check valve 330 and the sealing member 332 at the time of inserting the insertion portion 202 into the coat pipe 302, the insertion portion 202 can easily be pushed toward the front end side without causing buckle-deformation of the front end portion.

The guide portion 318 is formed of a hard member such as hard resin and metal, as in the case of the rigid portion 312 and the inner pipe portion 326. The guide portion 318 may be configured integrally with the inner pipe portion 326, and may be configured separately. In the latter case, the guide portion 318 and the inner pipe portion 326 are coupled with adhesives, solder and the like. It should naturally be understood that the rigid portion 312, the inner pipe portion 326, and the guide portion 318 may be configured integrally.

A conical introduction portion 320 having an inner diameter larger than that of the guide portion 318 is integrally provided on the base end side of the guide portion 318. An opening 334 for inserting the needle light 200 and the inner needle 304 into the coat pipe 302 is formed on an end face of the base end side of the introduction portion 320, and the opening 334 is configured to communicate with the insertion passage 322. The introduction portion 320 is formed gradually expanded toward the base end side, so that the needle light 200 and the inner needle 304 can easily be guided to the insertion passage 322 from the opening 334 of the introduction portion 320.

In the present embodiment, the trocars 718 and 704 (see FIG. 1) which are guide members for guiding the endoscope 100 and the treatment tool 720 into the body cavity are used. Publicly known trocars are used as the trocars 718 and 704, and so a description of their configuration is omitted. General trocars are made up of a coat pipe and an inner needle as in the above-described trocar 300, and includes a type of trocar which is stuck into a body cavity through a region partially incised with a scalpel and the like, and a type of trocar which is stuck into a body cavity directly from a body surface skin without any incision or with very small incision. Any of these types can be used.

[Method for Placing Body-Cavity Insertion Instruments]

The medical observation system 10 in the present embodiment configured as described above is used for laparoscopic surgery for treatment of an abdominal cavity that is one of the body cavities of a patient. A detailed description is now given of a method for placing in an abdominal cavity that is a body cavity of a patient the body-cavity insertion instruments (endoscope 100 and needle light 200) of the medical observation system 10 in the present embodiment for laparoscopic surgery with reference to FIG. 5 to FIG. 12C.

Figure 7:
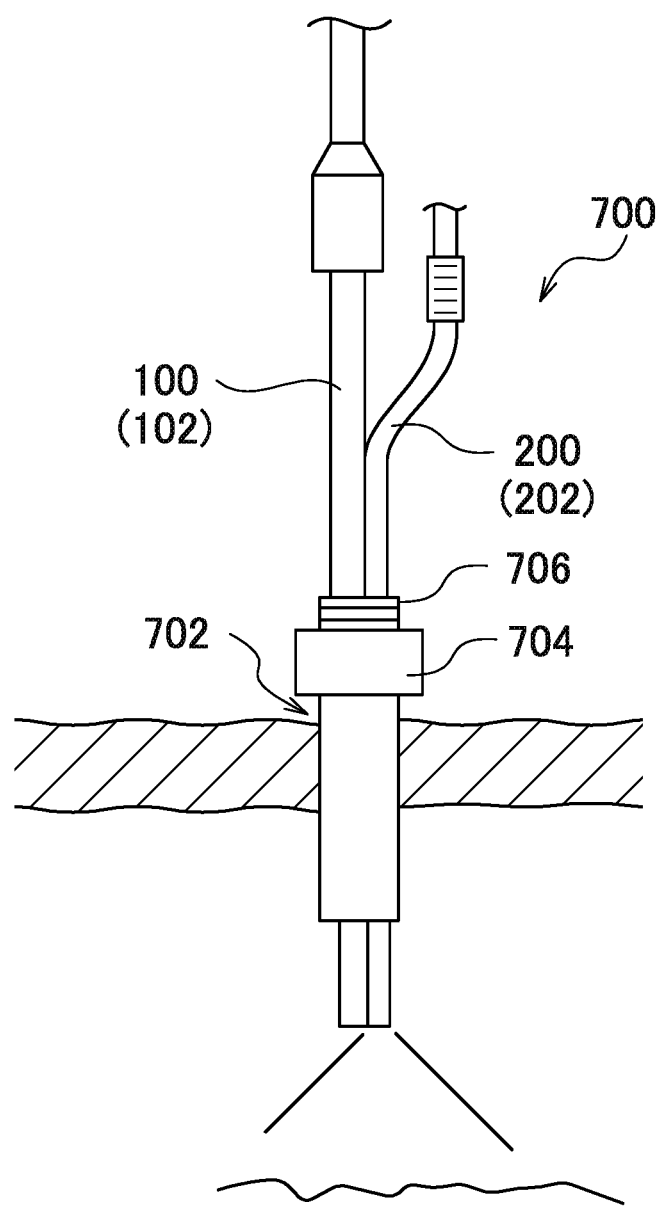
FIG. 7 is a cross sectional view schematically showing the body-cavity insertion instruments being inserted into an abdominal cavity.

FIG. 5 is a flowchart showing procedures for inserting into the abdominal cavity the body-cavity insertion instruments constituting the medical observation system 10 of the present embodiment. FIGS. 6A to 6D are plan views schematically showing the body-cavity insertion instruments being inserted into the abdominal cavity. FIG. 7 is a cross sectional view schematically showing the body-cavity insertion instruments being inserted into the abdominal cavity. It is to be noted that a series of steps shown in FIG. 5 are steps in consideration of low invasiveness in addition to safety.

First, as shown in FIG. 6A and FIG. 7, a scope unit 700 integrating the insertion portion 102 of the endoscope 100 and the insertion portion 202 of the needle light 200 is inserted into an abdominal cavity through a first opening (insertion hole) 702 formed on an abdominal wall (Step S10 of FIG. 5).

The first opening 702 is an opening formed in an abdomen (for example, umbilical region) of a patient for inserting treatment tools, such as forceps, into the abdominal cavity. A trocar 704 (for example, 5-mm forceps trocar) of a size corresponding to an external diameter of a treatment tool is inserted through the first opening 702, and the scope unit 700 is inserted into the abdominal cavity through the trocar 704.

In general laparoscopic surgery, at least one set of 5-mm forceps is needed. Step S10 of FIG. 5 is a technique step using the 5-mm forceps trocar. By inserting a 2.9-mm scope and a 2.1-mm needle light (2.9+2.1=5 mm) together into the 5-mm forceps trocar, less invasive preparation (trocar placement) for treatment can be performed without forming an unnecessary opening (insertion hole) on the abdominal wall.

Figure 8:
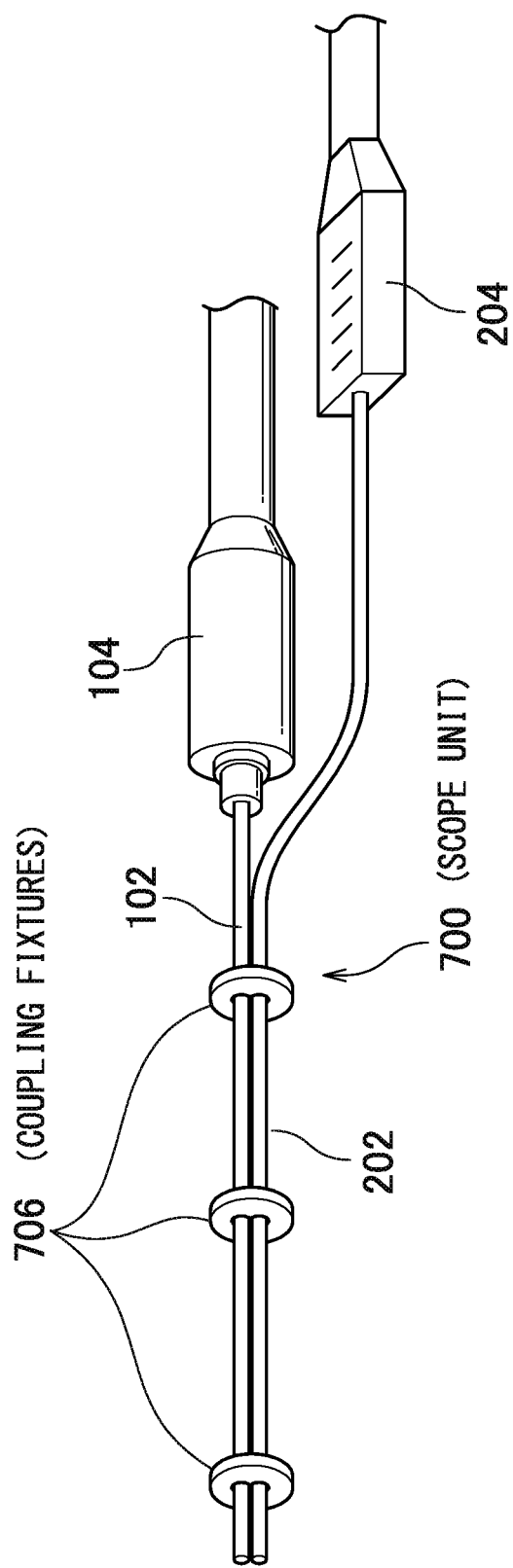
FIG. 8 is a schematic view showing a scope unit.
Figure 9:
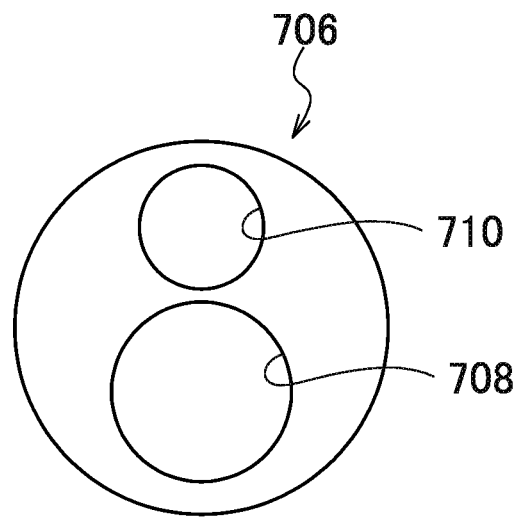
FIG. 9 is a plan view showing a configuration example of coupling fixtures.

FIG. 8 is a schematic view showing the scope unit 700. FIG. 9 is a plan view showing a configuration example of coupling fixtures 706. As shown in FIG. 8, the scope unit 700 is configured by integrating the insertion portion 102 of the endoscope 100 and the insertion portion 202 of the needle light 200 using a plurality of coupling fixtures (retaining members) 706 placed along with a longitudinal direction of the insertion portion 102 of the endoscope 100. Each coupling fixture 706 is configured for the respective insertion portions 102 and 202 to be slideable along the longitudinal direction of these portions.

The coupling fixture 706 is constituted of a thin-plate disc-like member made of, for example, a resin material such as plastic. Two through holes 708 and 710 different in inner diameter are formed in the coupling fixture 706. Out of these through holes 708 and 710, the first through hole 708 with a larger inner diameter is a hole portion for inserting the insertion portion 102 of the endoscope 100, and the inner diameter of the first through hole 708 is slightly larger than the external diameter of the insertion portion 102 of the endoscope 100. The second through hole 710 with a smaller inner diameter is a hole portion for inserting the insertion portion 202 of the needle light 200, and the inner diameter of the second through hole 710 is slightly larger than the external diameter of the insertion portion 202 of the needle light 200.

The insertion portions 102 and 202 are inserted through the respective through holes 708 and 710 of a plurality of the thus-configured coupling fixtures 706, and in this state the coupling fixtures 706 are placed side by side at specified intervals along with the longitudinal direction of the insertion portion 102 of the endoscope 100 as shown in FIG. 8. As a result, the insertion portion 102 of the endoscope 100 and the insertion portion 202 of the needle light 200 are integrated with their shaft directions parallel to each other and their shafts being close to each other.

If the scope unit 700 integrally formed as described above is inserted into the trocar 704, the respective coupling fixtures 706 come into contact with the end face of the base end side of the trocar 704 and are piled on top of each other without entering into the trocar 704 as shown in FIG. 7. The insertion portion 102 of the endoscope 100 and the insertion portion 202 of the needle light 200 are guided into the abdominal cavity while being parallel to each other with the trocar 704. Therefore, by inserting the scope unit 700 integrally configured with a plurality of the coupling fixtures 706 into the trocar 704, even the endoscope 100 without an illumination means can be guided safely and easily into the abdominal cavity.

The configuration of the coupling fixtures 706 is not limited to the configuration shown in FIG. 9. For example, configurations shown in FIGS. 10, 11A and 11B may also be employed.

Figure 10:
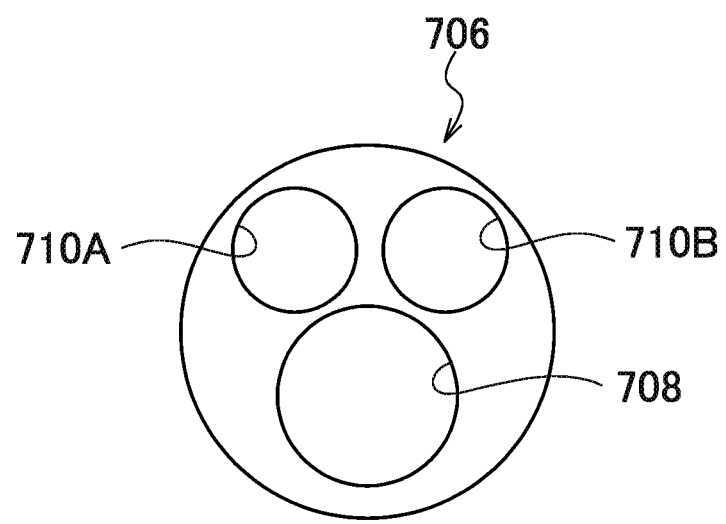
FIG. 10 is a plan view showing another configuration example of the coupling fixtures.

FIG. 10 is a plan view showing another configuration example of the coupling fixtures 706. As shown in FIG. 10, the coupling fixture 706 has a plurality of second through holes 710A and 710B formed therein. According to this configuration, the insertion portions 202 of a plurality of the needle lights 200 can be integrated with the insertion portion 102 of the endoscope 100. As a consequence, it becomes possible to secure desired brightness when illumination light from only one needle light 200 cannot provide sufficient brightness. It is to be noted that the number of the second through holes 710 is not limited to two but may be three or more. Moreover, a plurality of the first through holes 708 may also be formed.

Figure 11A:
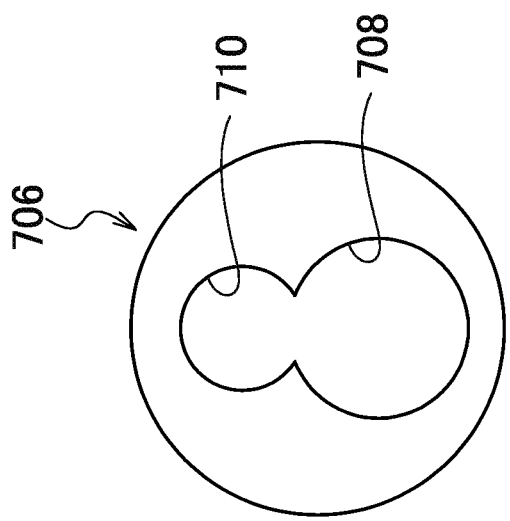
FIGS. 11A and 11B are plan views showing still another configuration example of the coupling fixtures.
Figure 11B:
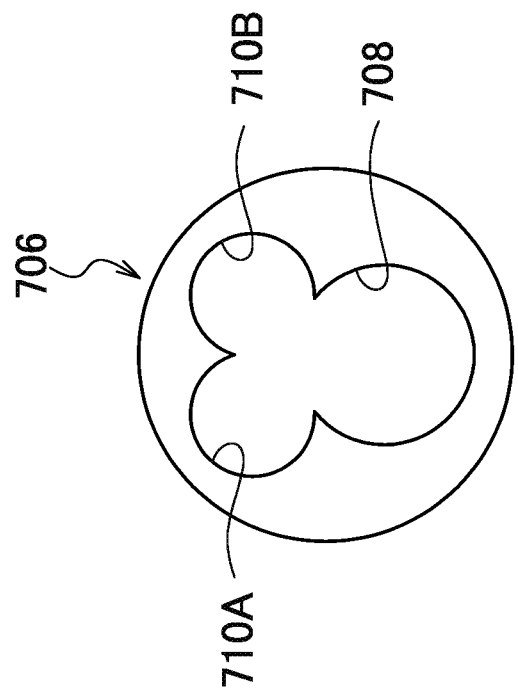

FIGS. 11A and 11B are plan views showing still another configuration example of the coupling fixtures 706. The configuration shown in FIG. 11A is in common with the configuration shown in FIG. 9 in that the first and second through holes 708 and 710 are formed but is different therefrom in that these through holes 708 and 710 are not separated nor independent from each other but are partially connected to each other. Similarly, the configuration shown in FIG. 11B is in common with the configuration shown in FIG. 10 in that the first through hole 708 and the second through holes 710A and 710B are formed, but is different therefrom in that these through holes 708, 710A, and 710B are not separated nor independent from each other but are partially connected to each other. With use of any one of these coupling fixtures 706, it is possible to integrate the insertion portion 102 of the endoscope 100 with the insertion portion 202 of the needle light 200.

In the present embodiment, the aforementioned coupling fixtures 706 are preferably used as a means to integrate the insertion portion 102 of the endoscope 100 with the insertion portion 202 of the needle light 200. However, without being limited thereto, integration may be achieved by, for example, collectively inserting the insertion portion 102 of the endoscope 100 and the insertion portion 202 of the needle light 200 into an oblong cylindrical insertion supporting tool (tube-like tool). Moreover, the insertion portion 102 of the endoscope 100 and the insertion portion 202 of the needle light 200 may integrally be bound with a string-like member with use of a treatment tool. However, an in the present embodiment, the configuration using the coupling fixtures 706 is the simplest and more preferable.

Referring again to FIG. 5, a description is continued. After the scope unit 700 is inserted into the abdominal cavity through the first opening 702, another needle light 200 is inserted into the abdominal cavity through a second opening 712 formed at a position different from the first opening 702 (for example, an upper right portion in the abdomen) as shown in FIG. 6B (Step S12 of FIG. 5).

The trocar 300 (needle light trocar) shown in FIG. 4 is inserted through the second opening 712, and the another needle light 200 is inserted into the abdominal cavity through the trocar 300. The same procedures apply to a later-described third opening 714.

Consequently, the insertion portions 202 of two needle lights 200 are now inside the abdominal cavity. Accordingly, even when one of the needle lights 200 is pulled out, the other needle light 200 can illuminate inside the body cavity, which can prevent the endoscope 100 without an illumination means from being put in an unobservable state.

Next, as shown in FIG. 6C, the insertion portion 202 of the needle light 200 is pulled out from the first opening 702 (Step S14 of FIG. 5).

Next, as shown in FIG. 6C, through a third opening 714 formed at a position different from the first and second openings 702 and 712 (for example, a central left portion in the abdomen), the insertion portion 202 of the needle light 200 pulled out from the first opening 702 is inserted into the abdominal cavity (Step S16 of FIG. 5).

Next, the insertion portion 102 of the endoscope 100 is pulled out from the first opening 702 (Step S18 of FIG. 5).

Next, as shown in FIG. 6D, the insertion portion 102 of the endoscope 100 is inserted through a fourth opening 716 formed at a position different from the first to third openings 702, 712 and 714 (for example, a central right portion in the abdomen) (Step S20 of FIG. 5).

The fourth opening 716 is an opening formed for inserting the insertion portion 102 of the endoscope 100 into the abdominal cavity. A trocar 718 (for example, 3-mm trocar) of a size corresponding to the external diameter of the insertion portion 102 of the endoscope 100 is inserted through the fourth opening 716, and the insertion portion 102 of the endoscope 100 is inserted into the abdominal cavity through the trocar 718.

Next, as shown in FIG. 6D, a treatment tool 720 such as 5-mm forceps is inserted into the abdominal cavity through the first opening 702 (Step S22 of FIG. 5).

By placing the insertion portion 102 of the endoscope 100 and the insertion portion 202 of the needle light 200 into the abdominal cavity of the patient in this way, specified examination, treatment and the like can be performed.

Now, a method for inserting the trocar 300 in the present embodiment is explained with reference to FIGS. 12A to 12C. FIGS. 12A to 12C are explanatory views showing a method for inserting the trocar 300.

First, as shown in FIG. 12A, the inner needle 304 is incorporated into the coat pipe 302 and in this state, the front end of the trocar 300 is inserted from a body surface skin that is an exterior surface of an abdominal wall to a specified depth position inside the abdominal wall along a direction (first direction) generally vertical to the body surface skin. In this case, the front end of the trocar 300 is inserted until the front end of the trocar 300 (the front end portion 308 of the inner needle 304 projected from the front end of the coat pipe 302 to be specific) reaches a middle position of a muscle layer (between the body surface skin and a peritoneum and preferably between a mid-position of the muscle layer and the peritoneum).

Next, the trocar 300 whose front end was inserted to the middle of the muscle layer is inclined as shown in FIG. 12B. More specifically, the trocar 300 is pushed down aslant so that the body portion 316 of the coat pipe 302 is closer to the body surface skin, with a longitudinal shaft direction of the insertion portion (the rigid portion 312 and the flexible portion 314) of the coat pipe 302 being in an oblique direction with respect to the body surface skin.

Next, as shown in FIG. 12C, while the trocar 300 is in the state of being inclined, the front end of the trocar 300 is inserted in a direction (second direction) oblique with respect to the body surface skin. As a consequence, the front end of the inner needle 304 inserted into the coat pipe 302 passes the peritoneum and is inserted to a depth position where the front end of the coat pipe 302 is inside the abdominal cavity. Then, the inner needle 304 is removed from the coat pipe 302, so that a pathway for guiding the insertion portion 202 of the needle light 200 into the abdominal cavity through the insertion passage 322 inside the coat pipe 302 is secured. Then, the insertion portion 202 of the needle light 200 is inserted into the insertion passage 322 of the coat pipe 302, so that the front end of the insertion portion 202 of the needle light 200 can be guided into the abdominal cavity.

According to the insertion method shown in FIGS. 12A to 12C, when the trocar 300 is stuck into the abdominal cavity, the front end of the trocar 300 is inserted to the middle position (middle of the muscle layer) inside the abdominal wall along the direction (first direction) generally vertical to the body surface skin, and then the front end of the trocar 300 is inserted from the middle position inside the abdominal wall into the abdominal cavity beyond the peritoneum along the direction (second direction) forming a more acute angle with the body surface skin than the first direction. In this case, as for the first direction, an angle of inclination (insertion angle) α1 with respect to the body surface skin is preferably 70 degrees to 110 degrees, more preferably 80 degrees to 100 degrees, and particularly preferably 85 degrees to 95 degrees. As for the second direction, an angle of inclination (insertion angle) α2 with respect to the body surface skin is preferably 60 degrees or less, more preferably 45 degrees or less, and particularly preferably 30 degrees or less.

By inserting the trocar 300 into the abdominal cavity in this way, the rigid portion 312 of the coat pipe 302 (a portion formed in a region which is enclosed with the body wall) receives larger resistance from the muscle layer as shown with arrows in FIG. 12B and FIG. 12C. Accordingly, as compared with the case where the trocar 300 is inserted without changing the insertion direction, the trocar 300 stuck into the abdominal cavity is reliably fixed. As a result, without being influenced by body motions and external vibrations, the needle light 200 inserted into the trocar 300 is stabilized, which makes it possible to prevent a target organ or other organs around the target organ from being damaged. Moreover, the needle light 200 inserted into the trocar 300 is fixed aslant in a stable state, so that illumination to the treatment target region can stably be emitted in a broader range. Further, if the needle light 200 can be fixed, operation thereof is unnecessary. This makes it possible to perform techniques without the necessity of adding operation of the needle light 200 to general laparoscopic surgery, i.e., without the necessity of increasing an operator to operate the needle light 200.

According to the present embodiment as described above, even in the case where the endoscope 100 does not have an illumination means, the insertion portion 102 of the endoscope 100 and the insertion portion 202 of the needle light 200 are inserted into a body cavity such as the abdominal cavity in accordance with the procedures shown in FIG. 5. As a result, it becomes possible to safely place the insertion portion 102 of the endoscope 100 and the insertion portion 202 of the needle light 200 at desired positions while constantly observing and illuminating the inside of the body cavity. Moreover, even when the number of openings formed on the body wall increases, the second to fourth openings 712, 714 and 716, which are openings for guiding the insertion portion 102 of the endoscope 100 and the insertion portion 202 of the needle light 200 into the body cavity, can be made smaller than the first opening 702. As a result, it becomes possible to make a postoperative scar less noticeable and to reduce the burden of the patient, so that low invasiveness can be achieved.

Moreover, since an opening can be formed at an arbitrary position corresponding to a treatment target region and access can be made thereto, operation is not constrained and therefore observation and treatment of the treatment target region can be facilitated. Moreover, it becomes possible to achieve easy access to a treatment target region where direct access from one opening is impossible, so that stable treatment can be performed.

Moreover in the present embodiment, the front end of the trocar 300 is inserted from the exterior surface of the body wall to the middle position inside the body wall along a first direction (direction generally vertically to the exterior surface of the body wall). Then, the insertion direction is changed to a second direction whose angle is acuter than that of the first direction, and in this direction the front end is inserted to the inside of the body cavity. As a result, the trocar 300 is reliably fixed with large resistance received from the body wall. This makes it possible to reliably fix the trocar 300 to the body wall by easy operation without causing increased costs and complicated configuration.

It is to be noted that the insertion method shown in FIGS. 12A to 12C is not only applied to the trocar 300, but is also applicable to medical instruments which can be pierced into body cavities.

Second Embodiment

FIG. 13 is a schematic view showing a configuration example of a needle light according to a second embodiment. As shown in FIG. 13, a needle light 200 according to the second embodiment is of a type which can be pierced into a body cavity (i.e., a type directly stuck in a body cavity from the body surface skin), including an outer pipe 246 with a sharp front end, and a light guide pipe 248 inserted into the outer pipe 246 so as to freely move back and forth.

The outer pipe 246 is constituted from, for example, a hard cylindrical body made of metal such as stainless steel and titanium. A front end portion thereof is formed to be opened and has an edge portion 250 provided to have a sharp blade surface cut aslant with respect to the shaft direction.

The light guide pipe 248 is an illuminating member capable of emitting illumination light for illuminating the inside of a body cavity from the front end portion. A light guide and an illumination optical system (each of which is unshown) are provided inside the light guide pipe 248.

A casing 252 formed to have a hollow inside is coupled to the base end side of the outer pipe 246. The casing 252 is made of a cylindrical tube member formed to be thicker than the outer pipe 246, and the light guide pipe 248 is inserted into the casing 252 so as to freely move back and forth. A through hole 254 for inserting the light guide pipe 248 is formed on a wall surface of the base end side of the casing 252. The through hole 254 is configured to have an inner diameter slightly larger than an external diameter of the light guide pipe 248 so that the light guide pipe 248 freely moves back and forth.

Inside the casing 252, a coil spring 256 is provided as a biasing means (biasing member) which biases the light guide pipe 248 in a front end direction with respect to the outer pipe 246. The coil spring 256 is wound around an outer periphery of the light guide pipe 248. A base end of the coil spring 256 is in contact with an inner wall surface 252a of the base end side of the casing 252. A front end of the coil spring 256 is in contact with to an end face of the base end side of a cylindrical fixing member 258 fixed to the light guide pipe 248. Consequently, the light guide pipe 248 is biased in the front end direction with respect to the outer pipe 246 with the biasing force of the coil spring 256.

A locking member 260, which can come into contact with an external wall surface 252b of the base end side of the casing 252, is provided on an outer peripheral portion of the base end side of the light guide pipe 248. The locking member 260, as shown in FIG. 13, comes into contact with the external wall surface 252b of the base end side of the casing 252 to lock the movement of the light guide pipe 248 in the front end direction in the state where the front end of the light guide pipe 248 is housed in the outer pipe 246 against biasing force of the coil spring 256.

Figure 14:
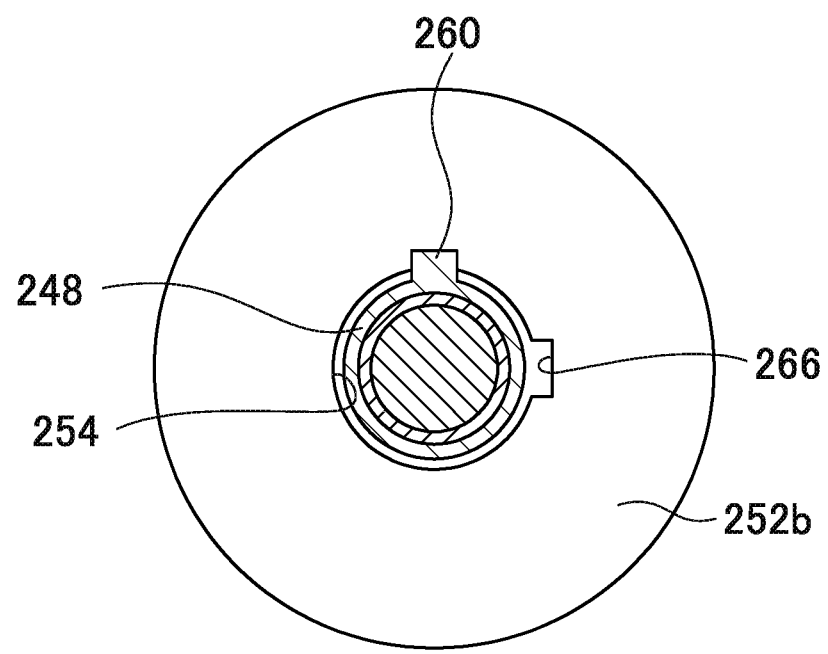
FIG. 14 is a cross sectional view taken along line 14-14 in FIG. 13.
Figure 15:
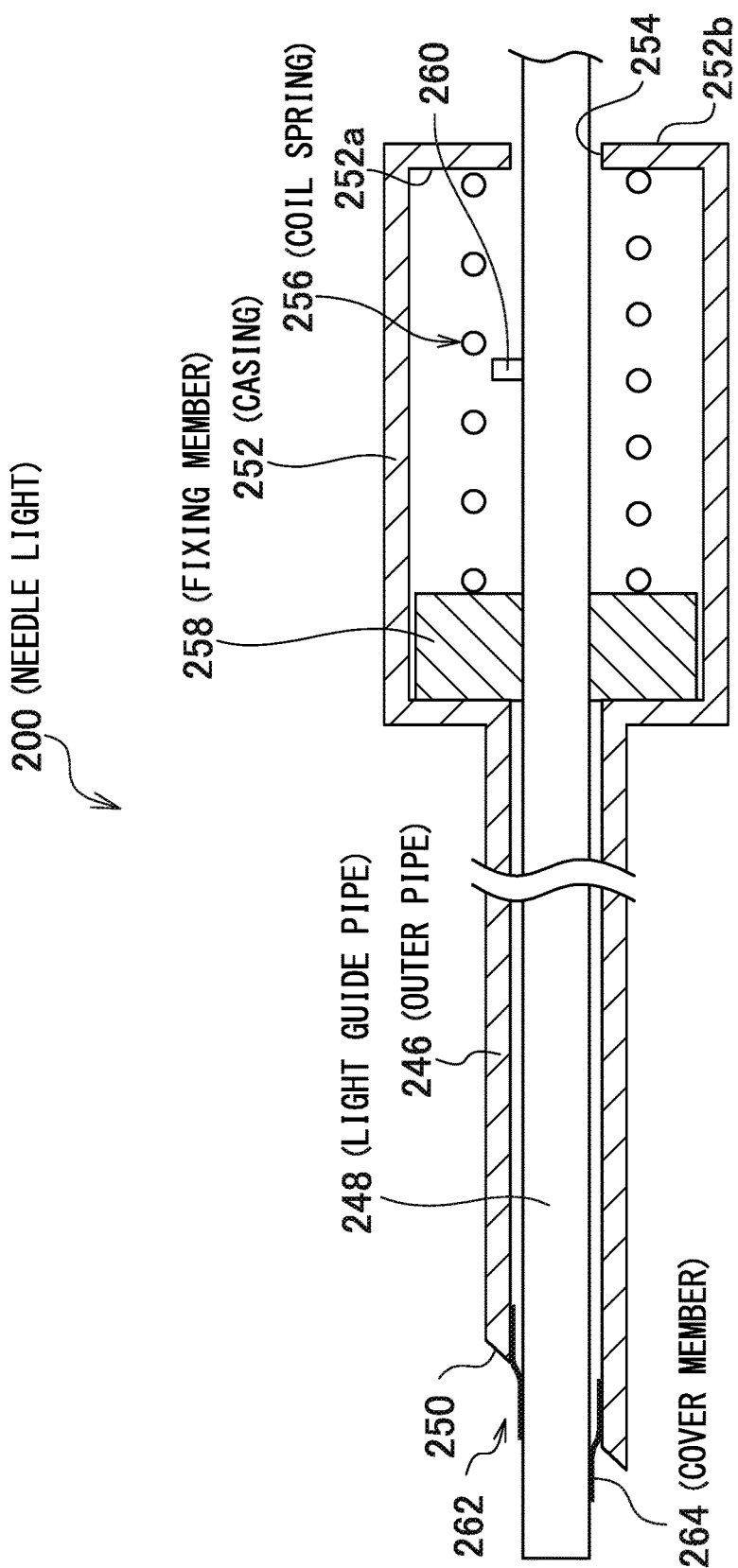
FIG. 15 is a schematic view showing a light guide pipe projecting from a front end of an outer pipe in a light guide shown in FIG. 13.

As shown in FIG. 14, the through hole 254 of the casing 252 is provided with an inserting groove 266 formed along a shaft direction at a phase position different from the locking member 260 of the light guide pipe 248. The inserting groove 266 is dimensioned so that the locking member 260 can be inserted therein. Accordingly, if the light guide pipe 248 is rotated relatively with respect to the casing 252 so as to coincide the phases of the locking member 260 and the inserting groove 266, the locking member 260 can pass through the inserting groove 266, by which the locked movement is unlocked. As a result, the light guide pipe 248 is made to be movable in the front end direction with the biasing force of the coil spring 256, so that the front end of the light guide pipe 248 is put in the state of projecting toward the front end side from a front end opening 262 of the outer pipe 246 as shown in FIG. 15.

The front end opening 262 of the outer pipe 246 is provided with a film-like (filmy) cover member (protective cover) 264 as a protective member for protecting the front end of the light guide pipe 248 housed in the front end opening 262. The cover member 264 is configured to have a breaking portion breakable when the front end of the light guide pipe 248 projects toward the front end side from the front end opening 262 of the outer pipe 246. The material and thickness of the cover member 264 are properly selected depending on the biasing force of the coil spring 256.

A description is now given of the functions of the present embodiment with reference to FIGS. 16A to 16C. FIGS. 16A to 16C are explanatory views showing the needle light 200 of the present embodiment being directly stuck into an abdominal wall from the body surface skin.

First, as shown in FIG. 16A, in the state where the front end of the light guide pipe 248 is housed in the outer pipe 246 and the movement of the light guide pipe 248 in the front end direction is locked by the locking member 260, an edge portion 250 at the front end of the outer pipe 246 is brought into contact with the body surface skin. In this case, the front end opening 262 of the outer pipe 246 is closed by the cover member 264.

Next, as shown in FIG. 16B, the movement of the light guide pipe 248 in the front end direction locked by the locking member 260 is unlocked, and the front end of the outer pipe 246 is stuck toward the abdominal wall from the body surface skin. At this time, although the light guide pipe 248 is in the state of being biased in the front end direction with the biasing force of the coil spring 256, the front end of the light guide pipe 248 receives pressing force from an abdominal wall toward the base end side through the cover member 264. Accordingly, the front end of the light guide pipe 248 is put in the state of being pushed into the outer pipe 246. In this case, since the front end opening 262 of the outer pipe 246 is closed by the cover member 264, adhering substances (fat, muscle, blood and the like) are prevented from adhering to the front end of the light guide pipe 248.

When the front end of the outer pipe 246 penetrates the abdominal wall and reaches the inside of the abdominal cavity as shown in FIG. 16C, pressing force received from the abdominal wall is lost. Therefore, the front end of the light guide pipe 248 breaks through the cover member 264 due to the biasing force of the coil spring 256 and is put in the state of projecting toward the front end side from the front end opening 262 of the outer pipe 246.

According to the present embodiment as described in the foregoing, when the front end of the outer pipe 246 penetrates the body wall and reaches a body cavity at the time of piercing the needle light 200 into the body cavity such as the abdominal cavity, the front end portion of the light guide pipe 248 breaks the cover member 264 with the biasing force of the coil spring 256, and automatically projects toward the front end direction from the front end opening 262 of the outer pipe 246. At this time, since the front end opening 262 of the outer pipe 246 is closed by the cover member 264 while the front end of the outer pipe 246 is penetrating the body wall, adhering substances (fat, muscle, blood and the like) are prevented from adhering to the front end of the light guide pipe 248 housed in the outer pipe 246. Therefore, it becomes possible to solve failures caused by the adhering substances adhering to the front end of the light guide pipe 248 and to pierce the needle light 200 into the body cavity by easy operation.

In the present embodiment, the cover member 264 is preferably made of an elastic membrane. When the front end of the outer pipe 246 is inside the body wall, it becomes possible to prevent the cover member 264 from breaking before the front end of the outer pipe 246 penetrates the body wall and reaches into the body cavity even if some pressure change occurs in a pressure difference between pressing force of a base end direction that the cover member 264 receives from a body wall and pressing force of a front end direction received from the front end of the light guide pipe 248. Therefore, it becomes possible to reliably prevent the adhering substances from adhering to the front end of the light guide pipe 248.

Although the present embodiment shows the configuration using the cover member 264 breakable with the biasing force of the coil spring 256, the present invention is not limited thereto, and a configuration using a cover member having an opening/closing portion that is openable and closeable such as a door and a valve may also be employed for example. In such a configuration as in the present embodiment, when the front end of the outer pipe 246 penetrates a body wall and reaches into a body cavity, the front end portion of the light guide pipe 248 automatically projects toward the front end direction from the front end opening 262 of the outer pipe 246 by putting the cover member 264 in an opened state with the biasing force of the coil spring 256.

Figure 17:
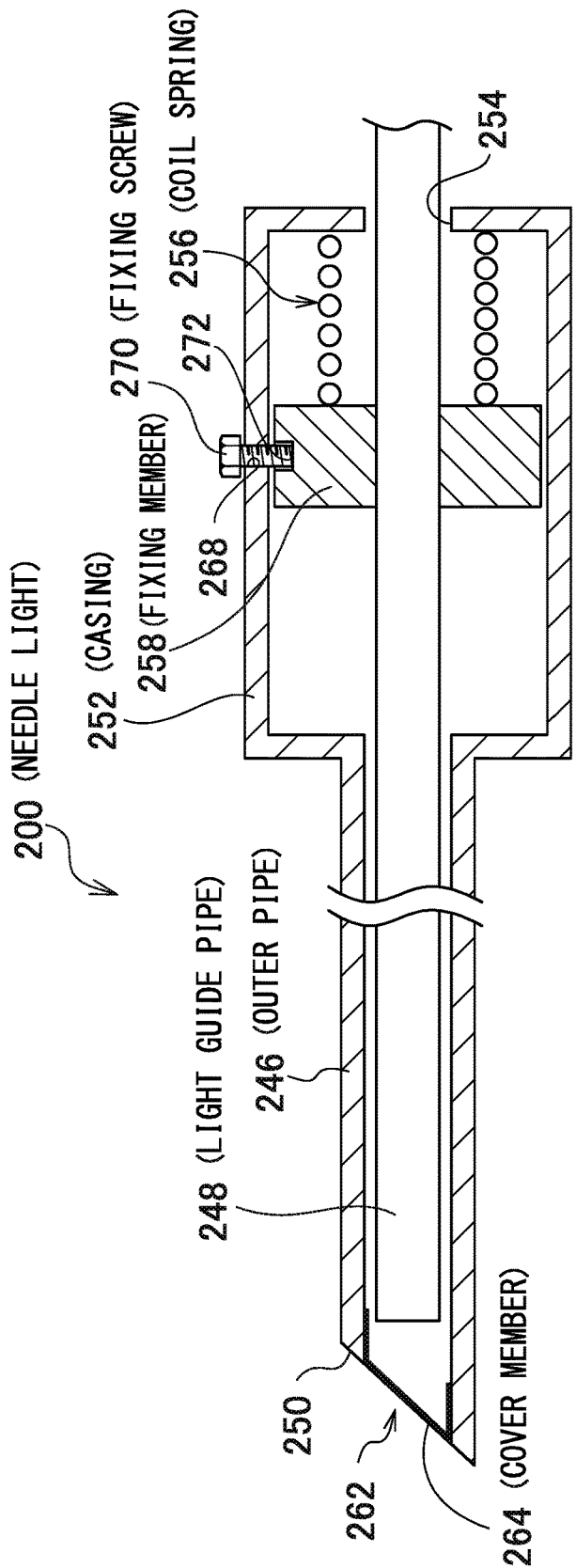
FIG. 17 is a schematic view showing another configuration example of the needle light according to the second embodiment.

Although, in the present embodiment, the locking member 260 provided on the outer peripheral portion of the base end side of the light guide pipe 248 is configured to come into contact with the external wall surface 252b of the base end side of the casing 252 as a means for locking the movement of the light guide pipe 248 in the front end direction against the biasing force of the coil spring 256, the present invention is not limited thereto, and a configuration shown in FIG. 17 may be employed for example.

FIG. 17 is a schematic view showing another configuration example of the needle light according to the second embodiment. In FIG. 17, component members in common with those in FIG. 13 are designated by identical reference numerals to omit a description thereof.

In the configuration shown in FIG. 17, a screw hole (female screw) 268 is formed by penetrating the outer peripheral surface of the casing 252. A fixing screw (male screw) 270 is screwed into the screw hole 268. When the fixing screw 270 is fastened, the front end of the fixing screw 270 is put in the state of projecting to an inner peripheral surface of the casing 252 and engaging with an engagement groove 272 formed on the outer peripheral surface of the fixing member 258. As a consequence, as in the case of FIG. 13, the movement of the light guide pipe 248 in the front end direction is locked in the state where the front end of the light guide pipe 248 is housed in the outer pipe 246 against the biasing force of the coil spring 256.

When the fixing screw 270 is loosened, the engagement between the front end of the fixing screw 270 and the engagement groove 272 is cancelled. As a result, the light guide pipe 248 is made to be movable in the front end direction with the biasing force of the coil spring 256, so that the front end of the light guide pipe 248 is put in the state of projecting toward the front end side from the front end opening 262 of the outer pipe 246 as in the case of FIG. 15.

According to the configuration shown in FIG. 17, operating the fixing screw 270 makes it possible to easily unlock the movement of the light guide pipe 248 locked in the front end direction.

The thus-configured needle light 200 of the present embodiment is preferably inserted into a body cavity such as an abdominal cavity by an insertion method shown in FIGS. 18A to 18C. FIGS. 18A to 18C are explanatory views showing the method for inserting the needle light 200.

First, as shown in FIG. 18A, the front end of the outer pipe 246 in the needle light 200 is directly inserted from the body surface skin to a specified depth position. At this point, the front end is inserted with the insertion direction of the outer pipe 246 being generally vertical to the body surface skin of the abdomen. In this case, the front end of the outer pipe 246 is inserted until it reaches the middle of a muscle layer (between the body surface skin and a peritoneum and preferably between a mid-position of the muscle layer and the peritoneum).

Next, the outer pipe 246 whose front end was inserted to the middle of the muscle layer is inclined as shown in FIG. 18B. That is, the shaft direction of the outer pipe 246 is made oblique with respect to the body surface skin.

Next, as shown in FIG. 18C, the front end of the outer pipe 246 is inserted in a direction oblique with respect to the body surface skin while the outer pipe 246 is in the state of being inclined. When the front end inside the outer pipe 246 is inserted past the peritoneum to a depth position inside the abdominal cavity, the front end of the light guide pipe 248 breaks through the cover member 264 and automatically projects from the front end opening 262 of the outer pipe 246. As a consequence, the inside of the abdominal cavity can be illuminated from the front end of the light guide pipe 248.

According to the insertion method shown in FIGS. 18A to 18C, for sticking the outer pipe 246 of the needle light 200 into the abdominal cavity, the front end of the outer pipe 246 is inserted to a middle position inside the abdominal wall (to the middle of the muscle layer) along the direction (first direction) generally vertical to the body surface skin, and then the outer pipe 246 is inserted along the direction (second direction) whose angle with the body surface skin is acuter than that of the first direction. At this time, preferable first and second angles of inclination (insertion angles) α1 and α2 of the first and second directions with respect to the body surface skin are similar to those of the first embodiment. By inserting the outer pipe 246 into the abdominal cavity in this way, the outer pipe 246 receives large resistance from the muscle layer as shown with arrows in FIG. 18B or FIG. 18C. Accordingly, as compared with a case where the outer pipe 246 is inserted without changing the insertion direction, the outer pipe 246 stuck into the abdominal cavity is reliably fixed. More specifically, since the needle light 200 is reliably fixed to the body wall, illumination to the treatment target region can stably be emitted, while damage of an organ can be prevented. Further, if the needle light 200 is fixable, operation thereof is unnecessary, and this makes it possible to perform techniques without the necessity of adding operation of the needle light 200 to general laparoscopic surgery, i.e., without the necessity of increasing an operator to operate the needle light 200.

In the foregoing, the method for inserting the medical instrument according to the present invention has been described in detail. However, it should be understood that the present invention is not limited to the examples disclosed and various modifications and arrangements which come within the meaning of the present invention are possible.

What is claimed is:

1. A method for inserting a medical instrument which is formed linearly along an axial direction and can be pierced into a body cavity, comprising:
   a first insertion step of inserting a front end of the medical instrument into a body wall along a first direction having a specified angle with respect to an exterior surface of the body wall; and
   a second insertion step of inserting, after execution of the first insertion step, the front end of the medical instrument into the body wall along a second direction whose angle with respect to the exterior surface of the body wall is acuter than that of the first direction, wherein
   the angle of the second direction with respect to the exterior surface of the body wall is 60 degrees or less.

2. A method for inserting a medical instrument which can be pierced into a body cavity, comprising:
   a first insertion step of inserting a front end of the medical instrument into a body wall along a first direction having a specified angle with respect to an exterior surface of the body wall; and
   a second insertion step of inserting, after execution of the first insertion step, the front end of the medical instrument into the body wall along a second direction whose angle with respect to the exterior surface of the body wall is acuter than that of the first direction,
   wherein the medical instrument is an illuminator for illuminating the inside of the body cavity including:
   a cylindrical outer pipe having a front end opening with a sharp front end;
   an illumination member inserted into the outer pipe movably along a shaft direction so as to be able to emit illumination light from a front end portion of the illumination member;
   a biasing member for biasing the illumination member in a front end direction with respect to the outer pipe;
   a locking member for locking movement of the illumination member in the front end direction in a state where the front end portion of the illumination member is housed in the outer pipe against a biasing force of the biasing member; and
   a protective cover for closing the front end opening of the outer pipe in a state where the front end portion of the illumination member is housed in the outer pipe by the locking member, and
   if a front end of the outer pipe is not in contact with a body tissue when locking by the locking member is unlocked, the front end portion of the illumination member pushes away the protective cover and projects from the front end opening of the outer pipe in the front end direction with the biasing force of the biasing member.

3. A method for inserting a medical instrument which has a longitudinal axis and can be pierced into a body cavity, comprising:
   a first insertion step of inserting a front end of the medical instrument into a body wall along a first direction having a first angle formed between the longitudinal axis of the medical instrument and a normal direction of an exterior surface of the body wall; and
   a second insertion step of inserting, after execution of the first insertion step, the front end of the medical instrument into the body wall along a second direction having a second angle formed between the longitudinal axis of the medical instrument and a normal direction of the exterior surface of the body wall, wherein the second angle is larger than the first angle.

4. The method for inserting a medical instrument according to claim 3, wherein
   the first insertion step is a step of inserting the front end of the medical instrument from the exterior surface of the body wall to a middle position inside the body wall.

5. The method for inserting a medical instrument according to claim 3, wherein
   the second insertion step is a step of inserting the front end of the medical instrument from a middle position inside the body wall to an inside of the body cavity.

6. The method for inserting a medical instrument according to claim 3, wherein
   the medical instrument is a guide pipe having an insertion passage for guiding a body-cavity insertion instrument into the body cavity.

7. The method for inserting a medical instrument according to claim 6, wherein
   the body-cavity insertion instrument is an illuminator for illuminating the inside of the body cavity.

8. The method for inserting a medical instrument according to claim 3, wherein
   the medical instrument is an illuminator for illuminating the inside of the body cavity.

9. The method for inserting a medical instrument according to claim 3, wherein the medical instrument has a cylindrical shape along an axial direction.

* * * * *

UNITED STATES PATENT AND TRADEMARK OFFICE
CERTIFICATE OF CORRECTION

PATENT NO. : 9,597,061 B2
APPLICATION NO. : 14/046630
DATED : March 21, 2017
INVENTOR(S) : Paul Curcillo Page 1 of 1

It is certified that error appears in the above-identified patent and that said Letters Patent is hereby corrected as shown below:

On the Title Page

At item (71) Applicant and item (73) Assignee, change "The Institute for Cancer Research, Philadelphia, PA (US)" to --The Institute for Cancer Research d/b/a Fox Chase Cancer Center, Philadelphia, PA (US)--.

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*